United States Patent [19]

Derkacs et al.

[11] Patent Number: 4,660,419
[45] Date of Patent: Apr. 28, 1987

[54] REFERENCE STANDARD FOR CALIBRATION OF ULTRASONIC ARRAYS

[75] Inventors: Thomas Derkacs, Mayfield Village; John Touhalisky, Eastlake, both of Ohio

[73] Assignee: TRW Inc., Cleveland, Ohio

[21] Appl. No.: 538,393

[22] Filed: Oct. 3, 1983

[51] Int. Cl.$^4$ ............................................ G01N 29/04
[52] U.S. Cl. ...................................... 73/622; 73/1 DV
[58] Field of Search ............... 73/1 DV, 622; 364/571

[56] References Cited

U.S. PATENT DOCUMENTS 4,173,139 11/1979 Conn .................................. 73/1 DV
4,462,082 7/1984 Thiele et al. ...................... 73/1 DV

FOREIGN PATENT DOCUMENTS 69248 4/1982 Japan ................................. 73/1 DV

OTHER PUBLICATIONS

Kyte et al., "A High—Speed Ultrasonic Testing Machine for Tubes," *The Radio and Electronic Engineer*, vol. 41, No. 5, May 1971, pp. 213-222.

"Use of DAC Curves and Transfer Lines to Maintain Ultrasonic Test Level Sensitivity" by Burkle et al. from Materials Evaluation, May 1983.

*Primary Examiner*—Stewart J. Levy
*Assistant Examiner*—John E. Chapman, Jr.
*Attorney, Agent, or Firm*—Kenneth G. Preston, Jr.

[57] ABSTRACT

An array of ultrasonic transducer (A) are disposed along a circular arc for examining tubular objects moving therethrough. A calibrating apparatus (B) includes a calibrating cylinder (22) having a plurality of calibrating flaws (24, 26) therein. A rotary positioning device (30) and an axial positioning device (40) adjust the relative spatial relationship of each calibration flaw and transducer. An ultrasonic control instrument (50) produces an echo signal having components corresponding to echoes received from the examined object. A computer (60) includes a gate adjustment control subroutine (66) which selectively separates a preselected component from the echo signal. A pulse amplitude measurement subroutine (64) measures the amplitude of the preselected echo signal component and, first, determines the peak amplitude of the component and, second, compares the amplitude of the component with a preselected standard. A position control subroutine (68), first, serially brings each calibration flaw generally into a preselected spatial relationship with each transducer and, second, adjusts the flaw/transducer spatial relationship until the pulse amplitude measurement subroutine detects the peak amplitude of the selected component. The spatial position of the peak amplitude is recorded in memory as an indication of the actual transducer location. A calibration subroutine (62) adjusts the gain and distance amplitude control adjustments of the ultrasonic instrument until the pulse amplitude measurement subroutine determines that the selected component matches the preselected standard.

13 Claims, 2 Drawing Figures

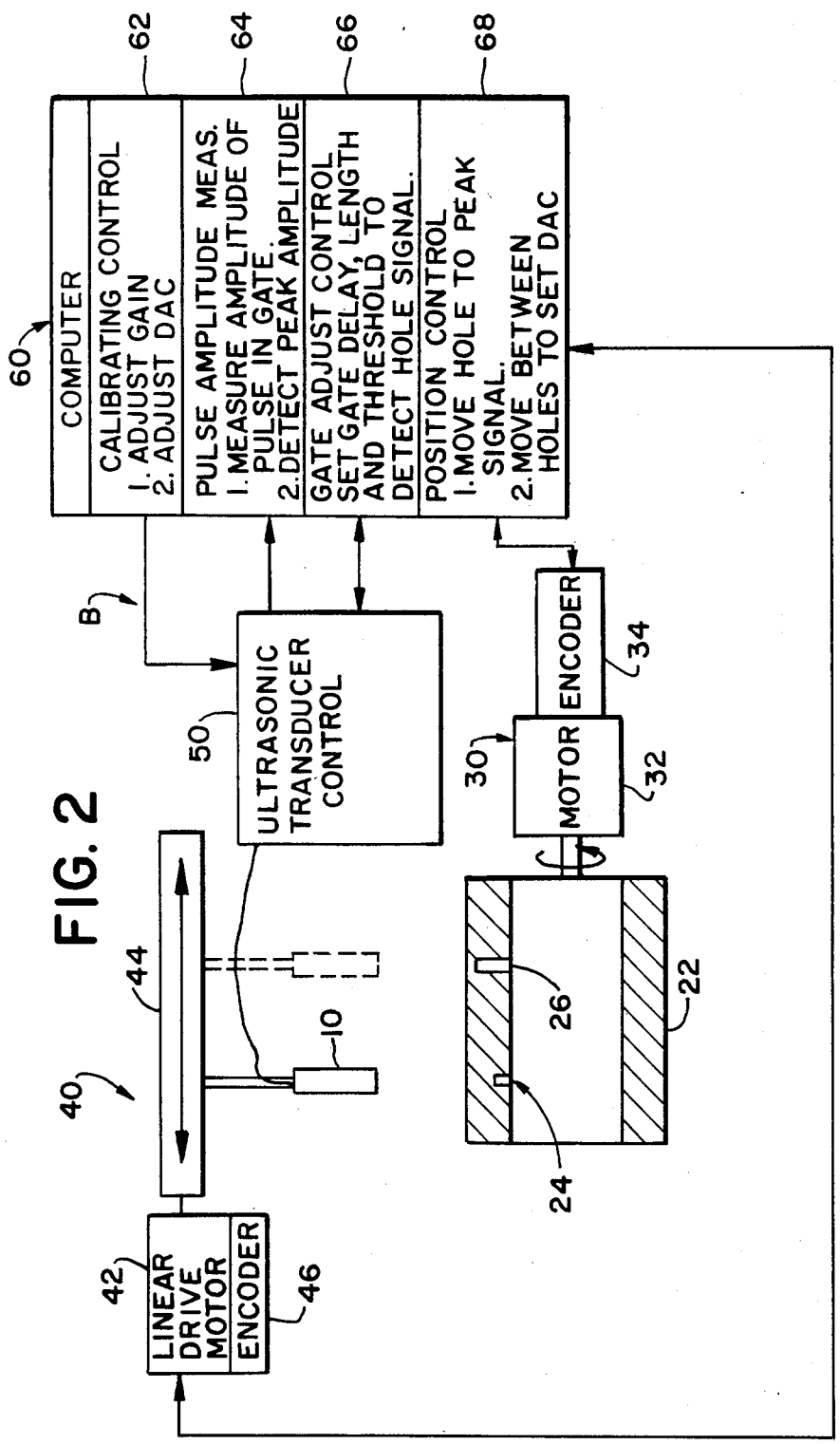

REFERENCE STANDARD FOR CALIBRATION OF ULTRASONIC ARRAYS

BACKGROUND OF THE INVENTION

The present invention relates to method and apparatus for the calibration of radiant energy detection apparatus. The invention finds particular application and will be described with particular reference to ultrasonic apparatus for detecting flaws in pipe and tubular goods. It is to be appreciated, however, that the invention also finds application in the calibration of inspection equipment useful in conjunction with other articles, particularly elongated or continuously formed articles including bars, rods, beams, sheets, and the like. In addition to ultrasonic flaw detection systems, the invention may also find utility in the calibration of other reflective and non-reflective radiant energy scanning systems.

Heretofore, the calibration of ultrasonic flaw detection systems has included positioning an ultrasonic transducer adjacent to each of a plurality of preselected, known flaws and monitoring the responses. Most commonly, each known flaw was a bored, flat bottomed hole of known depth. When monitoring each preselected flaw, the ultrasonic detection system was expected to produce a corresponding preselected, known response. Conventionally, the ultrasonic detection system included a gain adjustment and a distance amplitude correction adjustment. If the actual response of the ultrasonic detection system varied from the corresponding preselected response, the gain and distance amplitude correction adjustments were varied until the actual response matched the preselected response. The next transducer was then positioned adjacent the flaws and its gain and distance amplitude correction were similarly adjusted. When calibrating an array of ultrasonic transducers, a plurality of substantially identical sets of flat bottom holes could be provided, one set for each transducer. However, it would be difficult and labor intensive to provide flat bottom holes of exactly the same size and depth. Further, it would be difficult to position all of the holes precisely in the same relative position to its corresponding transducer. Any deviation in the size or location of a hole would create an error in the calibration of the corresponding transducer and degrade the accuracy of the results.

Commonly, pipe for oil well drilling, pipe and tubing for nuclear plants, and the like were tested for flaws at the steel mill and again in the field at the installation site. The physical movement of the inspection apparatus between installation sites as well as changes in temperature, humidity, altitude or barometric pressure, and the like necessitated regular recalibration of the inspection apparatus. Heretofore, the pipe has been inspected with gamma rays, electromagnetic fields, and other forms of penetrating radiant energy. The degree of attenuation of gamma radiation passing from a radiation source inside the pipe to one or more radiation detectors on the outside of the pipe provided an indication of flaws, concentricity, wall thickness, and other pipe characteristics. Variations in a magnetic field through which a metal pipe was passing provided an indication of variations in the magnetic susceptibility of the pipe caused by flaws and the like. Ultrasonic detection systems were commonly used in conjunction with the gamma ray and electromagnetic flaw detectors. Specifically, any area possessing a possible flaw was denoted or marked during gamma radiation or electromagnetic examination. Thereafter, an inspector using a hand held ultrasonic probe inspected the denoted area. In this manner, the ultrasonic probe provided a more detailed indication of the flaw initially detected by the relatively coarse gamma ray or electromagnetic flaw detector.

One of the problems with gamma radiation and electromagnetic pipe flaw detectors is that they are relatively insensitive to small flaws. This tends to degrade their ability to determine the exact position and nature of a detected flaw. The use of a hand held ultrasonic probe to more accurately examine the nature and position of a flaw is relatively slow and labor intensive.

The present invention contemplates a new and improved flow detection calibration method and apparatus for radiant energy detection systems.

SUMMARY OF THE INVENTION

In accordance with the present invention, a method of calibrating individual ultrasonic transducers of an array of such transducers is advantageously provided. The method includes positioning the transducer array at a predetermined position adjacent a calibration structure, e.g., a cylinder which includes at least one predetermined calibration characteristic such as a flaw or the like. The calibration characteristic is brought serially into a preselected spatial relationship with each transducer. While the flaw is in the preselected spatial relationship with a transducer, the transducer is pulsed and ultrasonic echoes are recieved. The output of the transducer is calibrated to bring it into conformity with a preselected standard response corresponding to the calibration characteristic.

In accordance with another aspect of the invention, there is provided a method for inspecting pipe or tubing at an installation site. In the method, relative movement between a circular array of radially oriented ultrasonic transducers disposed circumferentially of a length of pipe and the length of pipe itself is effected longitudinally of the array. A calibration cylinder, which includes rotational drive means is cooperatively positioned with the circular array. The calibration cylinder is rotated by the drive means to bring a calibration flaw substantially into a preselected spatial relationship serially with each of the transducers. While each transducer is in the preselected spatial relationship, it is pulsed and echoes from the flaw are monitored. The output of the transducer is calibrated to a preselected standard such that the outputs of all the transducers comprising the array are calibrated to produce a common output in response to the calibration flaw.

According to yet another aspect of the invention, there is provided a method of calibrating a radiant energy flaw detection apparatus which includes an array of radiant energy detectors. A calibration standard having a flaw at a predetermined position is cooperatively disposed with the transducer array. The standard is rotated serially to bring the flaw generally into a preselected spatial relationship with each of the detectors. The detector which is generally in the preselected spatial relationship with the flaw is caused to receive radiant energy that has interacted with the flaw. The output of the detector is monitored for a preselected component and the relationship between the flaw and detector is adjusted until the preselected component is optimized. Upon optimizing the component, the output of the detector is calibrated to a preselected standard.

Each detector in the array is serially calibrated in this manner to the same standard.

According to another aspect of the invention, an apparatus for calibrating each radiant energy detector in an array is provided. A flawed structure having at least one flaw at a predetermined position is adapted to be cooperatively positioned relative to the array. An indexing means serially brings the flaw into a preselected spatial relationship with each transducer of the array. A calibrating means calibrates the response of the transducer in the preselected spatial relationship with the calibration flaw.

In accordance with yet another aspect of the invention, there is provided an apparatus for calibrating each ultrasonic transducer in an array of such transducers. A calibration structure which has at least one flaw at a predetermined location is positionable adjacent each transducer in the array. A positioning means brings the calibration structure flaw and each transducer into a preselected spatial relationship. A computer means is operatively connected with an ultrasonic transducer control means and the positioning means. The ultrasonic transducer control means pulses the ultrasonic transducer in the preselected spatial relationship with the flaw and converts ultrasonic echoes into an echo signal. The computer includes position control means for selectively causing the positioning means to position the calibration structure serially in the predetermined relationship with each transducer. The computer means further includes pulse amplitude means for detecting optimization of a preselected component of the echo signal. The position control means adjusts the relative spatial relationship between the calibration structure and the flaw until the preselected component of the echo signal is optimized. The computer means further includes calibrating means for calibrating gain and distance amplitude control parameters such that the preselected echo signal component of each transducer is calibrated to a preselected standard.

One advantage of the present invention resides in the automatic and accurate calibration of an array of ultrasonic or other radiant energy transducers or detectors.

Another advantage of the invention is that it enables pipe or tube sections to be fully inspected with ultrasonic inspection equipment, even at an installation site.

Yet another advantage is that the invention facilitates calibration of a plurality of ultrasonic transducers with precise uniformity.

Still further advantages and benefits of the invention will become apparent upon a reading and understanding of the following detailed description.

BRIEF DESCRIPTION OF THE DRAWINGS

The invention may take form in various steps and arrangements of steps or in various parts and arrangements of parts, a preferred embodiment of which is shown in the drawings which form a part hereof and wherein.

DETAILED DESCRIPTION OF THE PREFERRED EMBODIMENT

Figure 1:
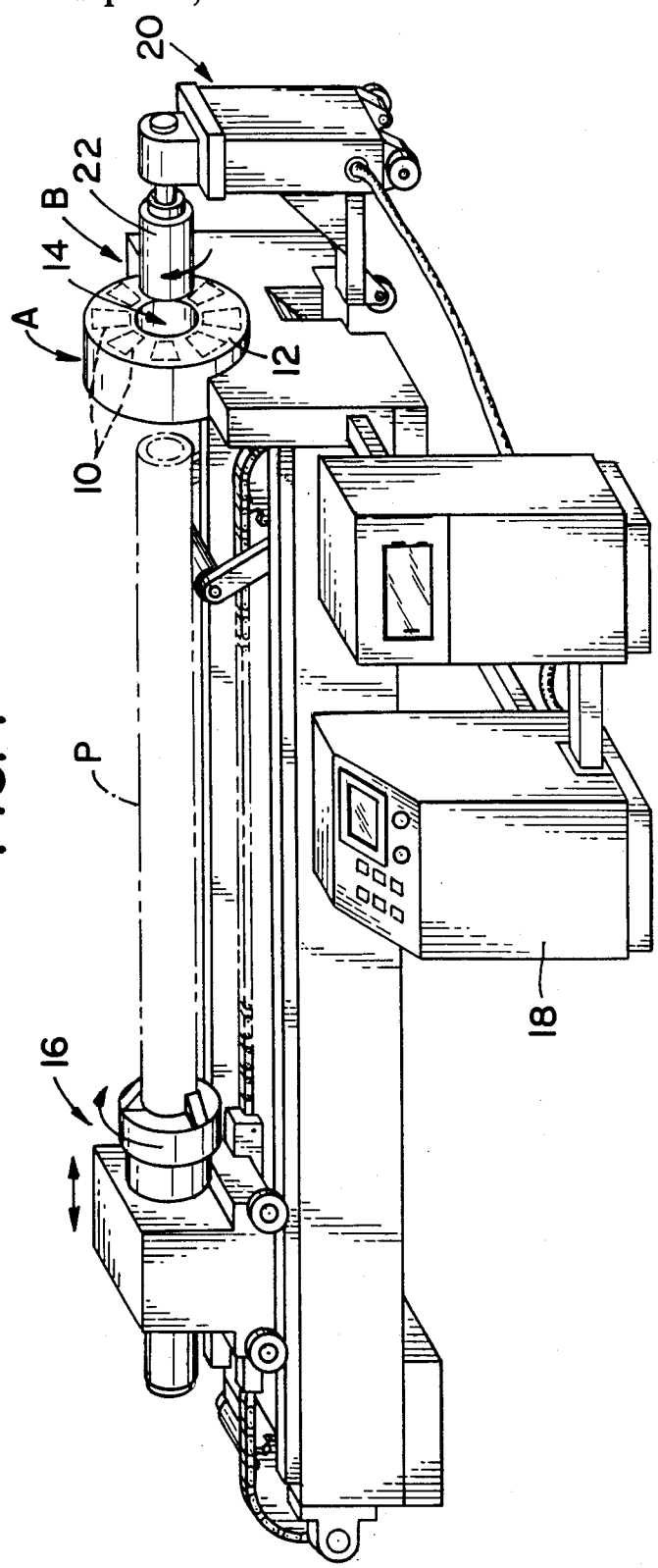
FIG. 1 is a somewhat schematic perspective view of an ultrasonic flaw detector for pipe including calibration apparatus formed in accordance with the present invention; and, FIG. 2 is a diagrammatic illustration of a computer implemented calibration apparatus for practicing the invention.

With reference to the drawings, FIG. 1 shows an array A of radiant energy detectors or transducers disposed for receiving an object to be inspected. A calibrating means B is selectively positionable adjacent the array for automatically calibrating each transducer in the array. In the preferred embodiment, the transducers comprise ultrasonic transducers 10 and the array is disposed along an arc such that circular objects are adapted to be passed therethrough for inspection. In particular, however, the array is configured to accommodate cylindrical or tubular objects.

The ultrasonic transducer array A includes a housing 12 which is adapted to be mounted or selectively positioned as required in the field, at a mill, or the like. The housing has a central opening 14 of circular cross-section which is compatible in diameter with the outside diameter of a pipe P to be tested. The ultrasonic transducers 10 are disposed inside the housing and are surrounded by an acoustic coupling medium, e.g., water, to provide an acoustic coupling between each transducer and the length of pipe being tested. A pipe feeding means 16 feeds the pipe through the transducer array in a controlled manner. Preferably, the pipe feeding means simultaneously rotates the pipe and advances it axially such that each transducer inspects a spiral path along the pipe. The details of feeding means 16 may take a number of different forms. Such details do not form a specific part of the invention and are not, therefore, described in detail herein.

To inspect a pipe or other object, the transducers are pulsed and receive ultrasonic echoes reflected from interfaces. In an unflawed piece of pipe, each ultrasonic transducer receives a first echo reflected from the pipe outer surface and another echo reflected from the inner surface. Each transducer produces an echo signal with a component or pulse corresponding to each received echo. Because the speed of ultrasonic signal propagation in the pipe is a known value, the time between these two echo components indicates the thickness of the pipe. The presence of a flaw produces one or more additional echoes between the inner and outer surface echoes. The time between the flaw echo and the inner and outer surface echoes and their relative intensities indicate the depth and the other physical properties of the flaw. An operator console 18 is included for providing a suitable warning, display, or the like of any detected flaws. Here, too, the specific details of console 18 do not form a part of the present invention.

With continuing reference to FIG. 1 and with particular reference to FIG. 2, each ultrasonic transducer examines a different spiral path along the pipe. It is highly desired during apparatus operation that the echo signal from a flaw be substantially the same regardless of which transducer or transducers are involved. Otherwise, the perceived depth and other physical properties of the flaw will vary with the transducer that detects it.

To that end and in accordance with the invention, the calibrating apparatus B is advantageously provided. This apparatus includes a moveable support stand or housing 20 which is adapted to be positioned in front of the array housing 12 in such a manner that a calibration structure, specifically a calibration cylinder 22, is positioned in the pipe receiving opening 14. The calibrating cylinder 22 has the same diameter as the pipe P to be inspected and has a plurality of preselected or known calibration characteristics.

With particular reference to FIG. 2 which illustrates the preferred arrangement here under discussion, the calibration characteristics are provided by calibrating flaws 24 and 26 disposed at predetermined locations along cylinder 22. These calibration flaws are defined by flat bottom bores each having a preselected diameter and depth, notches, spherical bottom holes, or the like, all generically denoted as well-like recesses, as may be appropriate to the transducer array being calibrated.

When a longitudinal acoustic wave from an ultrasonic transducer disposed normal to the cylinder strikes the flat bottom of the bore, an ultrasonic echo is reflected back toward the transducer which produces a bore bottom echo component of the echo signal. The elapsed time between the bore bottom echo signal component and either the inner or outer surface echo signal component is indicative of the depth of the bore or the thickness of the test cylinder between the bottom of the bore and the opposite surface. It is to be appreciated that longitudinal acoustic waves may also be reflected from the side walls of the bore causing the transducer to produce corresponding echo signal components, particularly when the transducer is not centered axially with the bore.

When a shear or surface wave from an ultrasonic transducer at an angle to the surface strikes the side walls of the notch or bore, an ultrasonic shear or surface wave echo is reflected. The elapsed time between transmission of the shear wave and receipt of the echo, i.e., between the transmission and echo components, is indicative of the distance from the transmitting transducer to the bore or notch and to the receiving transducer. Again, additional echo components may be produced by waves reflected from the bore bottom and other positions of the notch or bore periphery.

With continued reference to FIG. 2, the calibrating cylinder 22 is mounted for rotation on suitable bearings (not shown). A first or rotational positioning means 30 controls the position of the calibration cylinder relative to a first coordinate. More specifically, means 30 controls the relative angular spatial relationship around a longitudinal axis between the calibration bores and each transducer of the array. The rotational positioning means includes a motor 32 which is operatively connected with an angular position encoder 34 and the calibrating cylinder. the angular position encoder produces an output signal indicative of the angular position of the calibrating cylinder, hence the angular position of the calibration flaws.

A second or axial positioning means 40 controls the spatial relationship relative to a second coordinate between the calibration flaws of the calibrating cylinder and each transducer of the array. In FIG. 2, the axial positioning means is illustrated as moving the transducer 10 axially of the calibrating cylinder. Equivalently, and as would be required for the FIG. 1 arrangement, the axial positioning means may move the calibrating cylinder 22 relative to the transducer array A. The axial positioning means includes a linear drive motor 42 and a linear drive train 44 which selectively moves each transducer 10 of the array axially thereof. An axial position encoder 46 produces an output signal indicative of the relative axial relationship of the transducer array and the calibrating cylinder, hence of the calibration flaws. The first and second positioning means have been described in terms of the preferred field of use, i.e., inspecting cylindrical or tubular objects. When the invention is used to examine non-cylindrical objects, the first and second positioning means may position the transducers and calibration structure along other coordinates. For example, to inspect a flat sheet or a rectangular object, both positioning means may be linear; to examine a sphere, both positioning means may be angular, and so forth.

Each ultrasonic transducer 10 is connected with an ultrasonic transducer control means such as a conventional ultrasonic instrument 50. The ultrasonic transducer control means selectively pulses each ultrasonic transducer causing it to generate an ultrasonic wave and receives the echo signal the transducer produces upon being stimulated with ultrasonic echoes. The ultrasonic instrument amplifies the echo signals and processes them in a conventional manner to provide a display showing physical properties of the pipe and any flaws therein. To calibrate the ultrasonic instrument and the array, gain and distance amplitude correction adjustments are commonly provided. The gain adjustment adjusts the amplitude of the echo signal and the distance amplitude control adjustment adjusts the relative amplitude of echo signal components attributable to earlier and later received echoes. The amplitude correction adjustment compensates for the attenuation of the acoustic waves as they pass through the pipe and interfaces in the calibration cylinder by amplifying the echo signal non-linearly. Specifically, it amplifies later received echo signal components proportionally more than earlier received components. The proportion is selected from the time differences between echo components of the different depth bores and through the distance amplitude control adjustment.

A computer means 60 is operatively connected with the first and second positioning means 30 and 40 and with the ultrasonic transducer control means 50 for automatically controlling the calibration of each transducer of the array. Briefly stated, the computer means causes each calibration flaw to be positioned generally in the preselected spatial relationship with a first transducer of the array, adjusts the spatial relationship for more accurate alignment, calibrates the transducer, and repeats the process for each transducer.

The computer means includes a calibrating means 62 for adjusting the gain and distance amplitude control (DAC) of the ultrasonic transducer control means 50. More specifically, the calibrating means operates the appropriate electrical or electromechanical devices for adjusting the gain and distance amplitude control parameters of the ultrasonic transducer control means to bring the echo signal or a component thereof within a preselected standard.

The computer means 60 further includes a pulse amplitude means 64 for measuring an echo signal component and comparing the component with a preselected condition. The pulse amplitude means which, in the preferred embodiment, includes a programmed subroutine is operatively connected with the transducer control means 50 to receive the echo signals therefrom. Appropriate analog-to-digital converters convert the amplitude of the analog echo signals to a digital echo signal. The preselected condition in a first operation of the pulse amplitude means 64 is optimizing, particularly maximizing, the amplitude of a preselected echo signal component, specifically the bore bottom component. When the preselected component is optimized, the optimized components are used by the calibration control means 62 for adjusting the gain and the distance amplitude control. Specifically, the transducer is pulsed and the echo signal, particularly the bore bottom component of the longitudinal wave, is compared with a preselected calibration standard. Similarly, the shear wave echo components from the notch or bore side walls are optimized and compared with preselected calibration standards. The optimized echo components are stored until each bore has been optimally positioned adjacent the transducer being calibrated so that their transmission time differences may be utilized in the distance amplitude control adjustment. If the calibration standard is met, an index signal is produced to bring another one of the calibration flaws and transducers generally to the preselected spatial relationship and the process is repeated until each transducer is calibrated with each flaw to meet the corresponding standard.

Comparing the entire echo signal with corresponding standards would be complex and difficult. To simplify this comparison, a gate adjustment control means 66 operates on the echo signal to separate the preseleced component. Specific to longitudinal wave transmission calibration, it selects the component of the echo signal which is attributable to echoes from the flat bottom of the calibration bore. Because the depth of the calibration bore and the speed of transmission of the ultrasonic pulse are known, the length of time between pulsing of the transducer and receipt of the flat bottom component can be readily determined. The gate means discards or blocks all echo signal components except those in a window to either side of the determined flat bottom echo time from reaching the pulse amplitude measurement means 64. This causes the pulse amplitude means to measure the flat bottom echo signal component and detect its peak during centering, and compare it to a calibration standard during gain and distance amplitude control adjustment. The gate adjustment means also blocks components with amplitudes below a selected minimum or threshold as being attributable to noise, minor variations in pipe composition, and the like.

The computer means further includes a position control means 68 including a preprogrammed computer subroutine for controlling the relative position of the calibration flaws and each transducer of the array. The position control means controls the rotary drive motor 32 and the linear drive motor 42 to position each calibration flaw successively in alignment with each ultrasonic transducer. The angular position encoder 34 and the axial position encoder 46 indicate the relative spatial relationship of each calibration flaw and transducer to the position control means. The computer position control means has a memory which stores the position of each transducer in the array and the position of each calibration flaw on the calibration cylinder. More specifically, the position control memory stores a plurality of relative positions between the cylinder and array in a preselected order. Each stored relative position places a selected calibration flaw in a selected spatial relationship with a selected transducer. The totality of stored positions is sufficient to bring each calibration flaw in each preselected relationship with each ultrasonic transducer. The position control means receives the index signal from the pulse amplitude means indicating a calibration adjustment has been completed. The index signal causes the position control means to retrieve the next stored flaw/transducer relationship from the memory and causes the rotary and linear motors to adjust the actual flaw transducer relationship accordingly.

Once the position controller positions the flaw and transducer generally in the preselected spatial relationship, the transducer is pulsed. The pulse amplitude measurement means 64 measures the amplitude of the echo signal component and stores it in a temporary storage memory. The position control means causes the rotary and linear positioning means to adjust the spatial relationship of the calibration flaw and transducer by small incremental distance. The transducer is again pulsed and the amplitude of the echo signal component is compared with the amplitude in the temporary storage memory. The larger of the two is stored and the position control means adjusts the relative spatial relationship of the flaw and the transducer in accordance with the spatial relationship that produced the larger pulse. This pulse and spatial relationship adjustment process is continued until the echo signal component is optimized, specifically until its amplitude is maximized. The maximization of the flat bottom wall echo signal, for example, indicates that the calibration bore and the transducer are axially centered. When the bore and a normally disposed transducer are centered, the centered position is recorded for later use in identifying the position of defects during an inspection. This determines the relative transducer spacings and positions which may be used as offsets in analysis of inspection results to locate defects more accurately and so that defects viewed by more than one transducer can be recognized as being at a single location. In the centered position, the calibration control means 62, the pulse measurement means 64, and the gate adjustment control means 66 are actuated to calibrate the transducer which is aligned with the calibration bore. Similarly, when the bore and an angularly disposed transducer are centered on a preselected relationship, the transducer is calibrated.

By way of example, in a calibration operation for a normally disposed longitudinal wave transducer, the calibration cylinder 22 is positioned in the array of transducers 10 with one of the calibration flaws substantially in axial alignment with the transducers of the array. The position control means 68 causes the calibration flaw to be positioned generally aligned with a first one of the transducers. The position control means 68 adjusts the rotary position of the calibration flaw in small incremental amounts until the bore bottom echo signal component received by the pulse amplitude measurement means 64 through the gate means 66 is maximized. The position control means then adjusts the axial spatial relationship of the flaw and transducer until the flat bottom echo signal component is again maximized. The order in which the rotary and axial positions are adjusted may, of course, be reversed. In this manner, the computer means adjusts the relative positions of the calibration bore and the ultrasonic transducer being calibrated until they are centered. Once centered in axial alignment, the calibration control adjustment means 62 adjusts the gain control of the ultrasonic instrument 50 until the bore bottom echo signal component received by the pulse amplitude means 64 through the gate means 66 is brought within the preselected standard. The echo signal is temporarily stored in memory for use in adjusting the distance amplitude control.

After adjusting the ultrasonic instrument with the first of the calibration bores, the position control means 68 causes a second calibration bore 26 to be generally positioned in alignment with the transducer being calibrated. The position control means and the pulse amplitude measurement means accurately center the calibration bore and the transducer. The calibration means and the pulse amplitude measurement means recalibrate the gain and calibrate the distance amplitude control from the difference in the echo signals from the two bores, particularly from the time between echo components attributable to the difference in bore depth. Additional calibration bores of still other depths or with other characteristics may also be aligned with the transducer being calibrated and the distance amplitude control and other calibrations readjusted. Further, each of the calibration bores may be positioned a plurality of times in alignment with each transducer for successively finer calibration adjustments. This same calibration process is repeated serially for each transducer. Analogously, the invention may be used with angularly oriented, shear wave transducers. Here, each transducer is roughly positioned, spatially adjusted for optimal relative spatial relationship to the calibration characteristic, the calibration adjusted, and the relative spatial relationship of the transducers recorded.

Other modes of operating the calibration system are also contemplated by the present invention. For example in one such mode, the position control means 68 causes the rotational positioning means 30 to rotate the calibrating cylinder 22 at a constant speed. After a selected number of revolutions, the position control means 68 causes the axial positioning means to increment the axial position of the calibrating cylinder 22.

All transducers are operated as the calibration cylinder rotates. In one mode, the peak amplitude of the echo from each transducer is recorded by the pulse amplitude means 64 without regard to the angular position of the cylinder. The calibrating means 62 adjusts the gain to make the peaks uniform. After axial incrementing of the calibrating cylinder to record the echo peaks from at least two defect depths, the distance amplitude control is adjusted. Optionally, the angular orientation of the cylinder when each peak amplitude is received by the gate means 66 may also be recorded. From the angular orientation data, the actual position of each transducer can be calibrated.

In this alternate mode of operation, the computer 60 stores and analyzes the data for all transducers at once. Further, the calibration takes place at the actual inspection speed used for the given pipe size.

The invention has been described with reference to the preferred embodiment. Obviously, modifications and alterations will occur to others upon a reading and understanding of the preceding detailed description. It is intended that the invention be construed as including all such alterations and modifications insofar as they come within the scope of the appended claims or the equivalents thereof.

Having thus described the invention, it is now claimed:

1. A method of calibrating individual ultrasonic transducers in an array of ultrasonic transducers, the method comprising:
    (a) positioning the transducer array and a calibration structure adjacent each other, said calibration structure having a plurality of different depth calibration wells at a predetermined locations thereon;
    (b) from a computer memory, retrieving a first spatial relationship indicative of a spatial relationship between one of the calibration wells and a first transducer of the array;
    (c) bringing the one calibration well and the first transducer to the retrieved spatial relationship;
    (d) pulsing the first transducer and converting ultrasonic echoes which are received into an echo signal;
    (e) adjusting the spatial relationship between the calibration characteristic and the first transducer until a preselected component of the echo signal meets a preselected condition;
    (f) in the computer memory, recording the spatial relationship at which the echo signal component meets the preselected condition;
    (g) adjusting gain and distance amplitude corrections to the echo signal;
    (h) cyclically repeating steps (b) through (g) for each of a plurality of the calibration wells, at least once for each transducer in the array and readjusting the gain and distance amplitude corrections each time, whereby the gain and distance amplitude corrections are calibrated toward optimal values with each cyclic positioning of one of the calibration wells in the preselected spatial relationship with each transducer.

2. The method as set forth in claim 1 wherein said preselected condition comprises maximizing the amplitude of the preselected component.

3. A method of inspecting pipe for flaws, the method comprising:
    (a) locating an arcuate array of ultrasonic transducers substantially coaxial with a length of pipe to be inspected and with individual transducers disposed radially thereof;
    (b) positioning a calibration cylinder having at least one calibration flaw therein axially of the array;
    (c) rotating the calibration cylinder to bring the calibration flaw substantially into a preselected spatial relationship with a first transducer of the array;
    (d) pulsing at least the first transducer which is in the preselected spatial relationship to the calibration flaw and receiving echoes from the calibration flaw, the first transducer producing an echo signal corresponding at least to echoes received from the calibration flaw;
    (e) adjusting the relationship between the flaw and the first transducer until a monitored component of the echo signal attributable to the flaw is maximized;
    (f) recording the spatial relationship at which the maximized calibration flaw echo component is monitored, such that the relative spatial relationship of the first transducer to the array is recorded;
    (g) calibrating such that the echo signal meets a preselected standard;
    (h) repeating steps (c) through (g) for each transducer in the array, whereby each transducer in the array is calibrated to produce a common echo signal in response to the echoes from the calibrated flaw;
    (i) subsequent to calibrating the transducers, passing the array and the length of pipe to be inspected coaxially of each other, pulsing the transducers, receiving ultrasonic echoes for inspecting the pipe, and determining a spatial position of each detected flaw in the inspected pipe relative to a spatial position of a corresponding echo receiving transducer; and,
    (j) adjusting each determined flow spatial position in accordance with the recorded relative spatial relationship of the corresponding echo receiving transducer for more accurate recognition of flaw locations.

4. A method of calibrating a radiant energy flaw detection apparatus which includes an array of radiant energy detectors disposed along a circular arc, the method comprising:
(a) positioning a calibration cylinder which has a calibration flaw at a predetermined position substantially coaxial to the detector array;
(b) rotating the cylinder to bring the calibration flaw generally into a preselected spatial relationship with a first of the detectors;
(c) causing the first of the detectors to receive radiant energy which has interacted with the calibration flaw, the detector producing an electrical signal indicative of the radiant energy received;
(d) monitoring a preselected component of the electrical signal and adjusting the spatial relationship between the calibration flaw and the detector until the preselected component is optimized;
(e) recording the spatial relationship at which the preselected component is optimized;
(f) upon optimizing the preselected component, calibrating to bring the electrical signal into conformity with a preselected standard;
(g) serially bringing the calibration flaw into the preselected spatial relationship with each successive detector and repeating steps (b) through (f), such that each detector is calibrated to the same standard; and,
(h) determining the relative spatial relationships between the detectors of the array and compensating for non-uniformly spaced and oriented detectors of the array during examination of workpieces to determine flaw locations more accurately.

5. An apparatus for calibrating each ultrasonic transducer in an array of ultrasonic transducers mounted in conjunction with a pipe feeding means for selectively feeding cylindrical products through the array, the calibrating apparatus comprising:
a cylindrical sleeve which is selectively positionable within the ultrasonic transducer array, the sleeve defining at least one calibration flaw therein;
rotating means for selectively rotating the cylindrical sleeve about an axis of rotation;
a movable support stand on which the rotating means and the cylindrical sleeve are mounted such that the cylindrical sleeve and the rotating means are transported as a unit as the cylindrical sleeve is positioned in the transducer array for calibration and displaced away from the transducer array to permit the cylindrical products to be fed therethrough for inspection; and,
calibrating means for automatically calibrating while each transducer is in a preselected spatial relationship with the calibration flaw.

6. The apparatus as set forth in claim 5 further including means for pulsing each transducer at least while it is generally in the preselected spatial relationship with the calibration flaw and converting echoes at least partially from the calibration flaw into an echo signal and further including means for detecting a preselected echo signal component.

7. The apparatus as set forth in claim 6 further including position control means for causing the rotating means to vary the spatial relationship between the transducer and the calibration flaw until the preselected echo signal component meets a preselected standard.

8. The apparatus as set forth in claim 7 wherein the calibration flaw includes a well-like area having a bottom wall portion and a side wall portion and wherein the preselected echo signal component corresponds to at least an echo from the bottom wall and wherein the preselected standard is maximizing the bottom wall echo signal component.

9. The apparatus as set forth in claim 7 wherein the cylindrical sleeve includes a plurality of calibration flaws, the rotating means serially positions each calibration flaw generally in the preselected spatial relationship with each transducer and adjusts the spatial relationship until the preselected echo signal component meets the preselected standard, and the calibration means readjusts the calibration while each transducer is in the preselected spatial relationship with each calibration flaw.

10. An apparatus for automatically calibrating the output of each ultrasonic transducer in an array of ultrasonic transducers mounted in conjunction with a pipe feeding means for selectively feeding cylindrical products through the array, the calibrating apparatus comprising:
a calibrating cylinder which is selectively positionable in the ultrasonic transducer array, the calibrating cylinder having a plurality of calibration flaws disposed at predetermined positions thereon;
rotating means for selectively rotating the calibration cylinder about an axis of rotation to selectively bring each calibration flaw generally into a preselected spatial relationship with each transducer;
a movable support stand on which the rotating means and the calibrating cylinder are mounted such that the calibrating cylinder and the rotating means are transported as a unit as the calibrating cylinder is positioned in the transducer array for calibration and displaced away from the transducer array to permit the cylindrical products to be fed therethrough for inspection;
ultrasonic transducer control means for selectively pulsing at least the transducer in the preselected spatial relationship with one of the flaws and converting received ultrasonic echoes into an echo signal; and,
a computer means operatively connected with the ultrasonic transducer control means and the rotating means, the computer means including:
position control means for controlling the rotating means to position the calibrating cylinder and the transducer array relative to each other such that each calibration flaw is brought serially generally into the preselected relationship with each transducer;
pulse amplitude means for detecting optimization of a preselected component of the echo signal from the transducer in the preselected spatial relationship with one of the calibration flaws;
said position control means adjusting the relative spatial relationship between the one flaw and the transducer array until the preselected echo signal component is optimized;
recording means for recording in computer memory each spatial relationship in which the preselected echo signal component is optimized; and,
calibrating means operatively connected with the ultrasonic transducer control means for adjusting gain and distance adjustment control parameters such that the preselected echo signal component is calibrated to a preselected standard.

11. The apparatus as set forth in claim 10 wherein the computer means further includes a gate adjustment control means for blocking receipt by the pulse amplitude means of components of the echo signal other than the preselected echo signal component.

12. The apparatus as set forth in claim 10 wherein the calibration flaws comprise a plurality of bores having a preselected depth to a bottom wall, and wherein the array of ultrasonic transducers are positioned along at least a segment of a circular arc.

13. The apparatus as set forth in claim 12 further including an axial position means for adjusting the relative axial relationship between the calibrating cylinder and the transducer array.

* * * * *